United States Patent
Kennedy

(10) Patent No.: US 7,275,035 B2
(45) Date of Patent: Sep. 25, 2007

(54) SYSTEM AND METHOD FOR SPEECH GENERATION FROM BRAIN ACTIVITY

(75) Inventor: Philip R. Kennedy, Duluth, GA (US)

(73) Assignee: Neural Signals, Inc., Atlanta, GA (US)

( * ) Notice: Subject to any disclaimer, the term of this patent is extended or adjusted under 35 U.S.C. 154(b) by 299 days.

(21) Appl. No.: 11/007,380

(22) Filed: Dec. 8, 2004

(65) Prior Publication Data

US 2005/0144005 A1   Jun. 30, 2005

Related U.S. Application Data

(60) Provisional application No. 60/527,943, filed on Dec. 8, 2003.

(51) Int. Cl.
*G10L 13/06* (2006.01)
*G10L 11/00* (2006.01)
*G10L 21/06* (2006.01)

(52) U.S. Cl. ........................ 704/271; 704/267

(58) Field of Classification Search ............ 704/1, 704/2, 271, 200, 500, 503
See application file for complete search history.

(56) References Cited

U.S. PATENT DOCUMENTS

| | | | |
|---|---|---|---|
| 4,736,751 A | | 4/1988 | Gevins et al. |
| 6,128,527 A | * | 10/2000 | Howard et al. ............. 600/544 |
| 6,996,261 B2 | * | 2/2006 | deCharms ................... 382/131 |
| 7,120,486 B2 | * | 10/2006 | Leuthardt et al. ........... 600/544 |
| 2002/0099412 A1 | | 7/2002 | Fischell et al. |
| 2002/0103429 A1 | | 8/2002 | deCharms |
| 2003/0023183 A1 | | 1/2003 | Williams |
| 2004/0267320 A1 | * | 12/2004 | Taylor et al. .................. 607/2 |
| 2005/0065427 A1 | * | 3/2005 | Magill et al. ................ 600/407 |
| 2005/0070810 A1 | * | 3/2005 | Kennedy ..................... 600/544 |
| 2005/0102144 A1 | * | 5/2005 | Rapoport ..................... 704/269 |
| 2006/0075883 A1 | * | 4/2006 | Thorne et al. ................ 84/616 |

\* cited by examiner

*Primary Examiner*—Tālivaldis Ivars Šmits
*Assistant Examiner*—Josiah Hernandez
(74) *Attorney, Agent, or Firm*—Bryan W. Bockhop; Bockhop & Associates, LLC

(57) ABSTRACT

In a method of assisting a subject to generate speech, at least one first neural impulse is sensed from a first preselected location in the subject's brain. A first preselected sound is associated with the first neural impulse. The first preselected sound is generated in an audible format. In an apparatus for assisting the subject to generate speech, at least one sensor senses a neural impulse in the subject's brain and generates a signal representative thereof. An electronic speech generator generates a phoneme in response to the generation of the signal. An audio system generates audible sounds corresponding to the phoneme based upon the signal received from the speech generator.

33 Claims, 2 Drawing Sheets

SYSTEM AND METHOD FOR SPEECH GENERATION FROM BRAIN ACTIVITY

CROSS-REFERENCE TO RELATED APPLICATION

This application claims the benefit of U.S. Provisional Application Ser. No. 60/527,943, filed Dec. 8, 2003, the entirety of which is hereby incorporated by this reference.

STATEMENT OF GOVERNMENT INTEREST

This invention was made with support from the U.S. government under grant number 1R43DC007050-01 awarded by the National Institutes of Health. The government may have certain rights in the invention.

BACKGROUND OF THE INVENTION

1. Field of the Invention

The present invention relates to medical systems and, more specifically, to a system for generating speech and other sounds based on neural impulses.

2. Description of the Prior Art

Locked-in syndrome is a condition in which the subject has little or no motor control of the muscles needed to generate speech. In such a subject, communication may be effected by sensing eye movements. In one communication method, the movement of the subject's eye is correlated to a table of letters displayed on a computer screen and the subject spells out words by looking at the letters that forth the words that the subject wants to communicate. The result may be fed into a speech generator, which makes sounds corresponding to the words indicated by the subject. Alternately, inputs other than eye movement, such as motor-neural impulses, may be used to facilitate communications. In such systems, the input may control a cursor that moves over letters or icons on a computer screen and if the cursor rests on a letter for a sufficient amount of time, then the letter is added to a string of letters that eventually forms a word.

Such systems are limited in that they take a considerable amount of time to generate even simple words and they require the subject to expend extra mental effort in determining which letters are needed and the location of the letters on the table.

The region of the brain associated with speech generation is referred to as "Broca's area." Generally, when one speaks, neuronal discharges form electrical spikes in the neurons in Broca's area. These discharges may be sensed from the local axons, where they are referred to as "action potentials." Several different action potentials may be sensed in one location, with each different action potential possibly corresponding to a different mental action.

Currently, no system measures neuronal discharges or action potentials in the brain and transforms them directly into sounds such as phonemes, the most fundamental sounds that form words. Generating phonemes directly from action potentials in Broca's area would result in nearly real-time generation of speech. Giving a subject the ability to generate speech in a natural way would greatly facilitate communication between the subject and the outside world.

Therefore, there is a need for a speech generation system and method that employs a real-time natural mental process for the generation of sounds.

SUMMARY OF THE INVENTION

The disadvantages of the prior art are overcome by the present invention which, in one aspect, is a method of assisting a subject to generate speech in which at least one first neural impulse is sensed from a first preselected location in the subject's brain. A first preselected sound is associated with the first neural impulse. The first preselected sound is generated in an audible format.

In another aspect, the invention is a method of assisting a subject to generate sounds in which a plurality of neural impulses is sensed from a plurality of locations in the subject's brain. A preselected sound is associated with a predetermined pattern of neural impulses. The preselected sound is generated in an audible format.

In another aspect, the invention is a method of enabling communication with a subject in which a functional MRI scan of the subject's brain is performed while the subject is executing a predetermined mental exercise so as to determine a first location in the subject's brain where neural activity occurs while the subject is executing the mental exercise. An electrode is implanted in the subject's brain at the first location. The subject is trained to associate a desire to express a predetermined phoneme with an action potential generated at the first location in the subject's brain. The action potential is sensed at the electrode. An audible sound corresponding to the predetermined phoneme is generated in response to the sensing of the action potential.

In yet another aspect, the invention is an apparatus for assisting a subject to generate speech based upon electrical activity in the brain. At least one sensor senses a neural impulse in the subject's brain and generates a signal representative thereof. An electronic speech generator generates a phoneme in response to the generation of the signal. An audio system generates audible sounds corresponding to the phoneme based upon the signal received from the speech generator.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
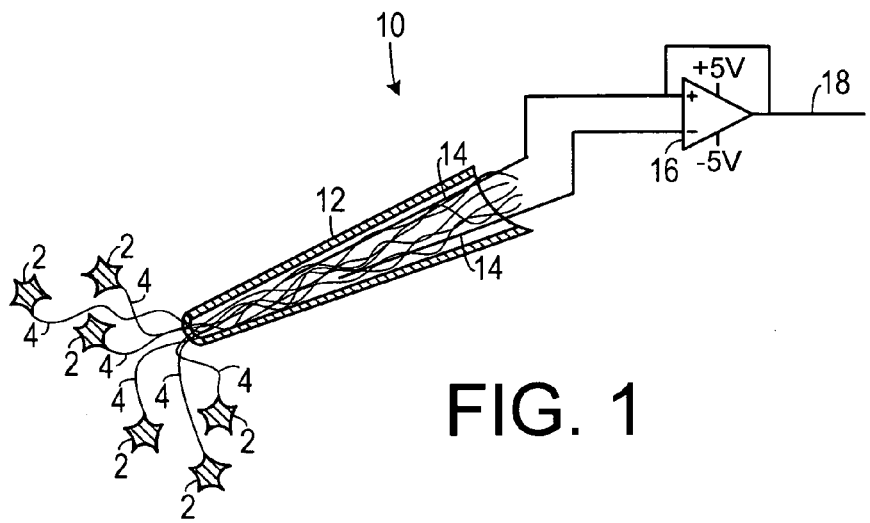
FIG. 1 is a schematic diagram of a neurotrophic electrode.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

The present invention is for a system and method that records neural activity in the brains of humans and uses this activity to drive a speech generator. Such a device requires no intermediate means of speech generation such as selection of icons or letters on spelling devices. Instead, activity from individual cortical neural signals is sensed via an FDA-approved neurotrophic electrode (or other suitable type of electrode), amplified, transmitted transcutaneously and processed using spike sorting software. The pulsed outputs of these processed neural signals drive a speech generator.

Generally, a subject's brain is mapped using functional MRI during a mental exercise performed by the subject to determine areas of local activity in the brain. At least one electrode is implanted in the brain in the areas of local activity and neural impulses (such as neuronal discharges or action potentials) are sensed at the electrodes. The subject is trained to generate specific neural impulses in response to imagining saying a specific sound, such as a phoneme. Once trained, when the subject generates a specific neural impulse, the electrode senses it and transfers it to a computer-controlled sound generator. The computer associates the neural impulse with a specific sound (such as a phoneme) and generates an audible version of the sound.

As shown in FIG. 1, one type of suitable electrode is the neurotrophic electrode 10, available from Neural Signals, Inc. of Atlanta, Ga. Such a neurotrophic electrode 10 includes a hollow glass cone 12 containing gold recording wires 14 that allow recording from axons 4 growing from neural cells 2 into the glass cone 12 under the influence of trophic factors. Changes in electrical potential between the recording wires 14 are input into an amplifier 16, which generates an output 18 corresponding to the change. One example of a neurotrophic electrode is disclosed in U.S. Pat. No. 4,852,573, which is hereby fully incorporated by reference. The electrode may be implanted in the subject's brain and transmitted to the computer via a transcutaneously embedded transmitter. Such a system is described in U.S. patent application Ser. No. 10/675,703, filed on 30 Sep. 2003 and entitled "Detecting Neural Signals and Using Same to Drive External Functions," which is hereby fully incorporated by reference.

Other electrodes may be used in the invention. For example, the Bionic Technologies "Utah" array of 10 by 10 pins has excellent recording characteristics, although it may not have a great amount of stability and may not have recordings beyond a few years. Other electrodes (both wired and wireless) and neural signal scanning apparatuses can likewise be used in the present invention as would be apparent to one of skill in the art.

The system may sense action potentials, local field potentials (which correspond to several action potentials added together), or other types of neural impulses, such as neuronal spikes and neuronal discharges.

Recording from this type of implanted neurotrophic electrode has produced action potentials that display robust signal-to-noise ratios over long time periods. The neurotrophic electrode has allowed paralyzed and mute (locked-in) subjects to control computers and thus communicate using computer generated speech. The neurotrophic electrode can utilize an FDA-approved (and biologically compatible) recording system that uses transcutaneous FM transmission of the amplified signals and thus no wires. Further, the neurotrophic electrode may be powered by air gap induction coils, obviating the need for batteries. In prior implementations, the neurotrophic electrode system was implanted in locked-in humans to provide them with control of a switch or a computer cursor, thus restoring communication (with or without synthetic speech generated from data input), Internet access, environmental control and so on. Its stability is due to the in-growth of neurites that become myelinated axons growing through a hollow glass tip of the electrode and connecting to the neuropil outside each end of the cone. These connections hold the electrode tip within the brain substance.

Figure 2:
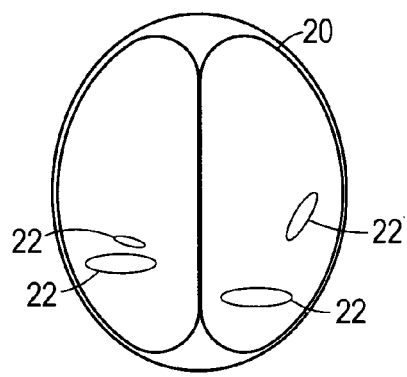
FIG. 2 is a schematic diagram of a brain.

As shown in FIG. 2, a functional MRI scan of the subject's brain 20 may reveal several areas 22 of activity when the subject performs a predetermined mental exercise. Such an exercise could include having the subject attempt to say a list of specific phonemes or other sounds.

Figure 3:
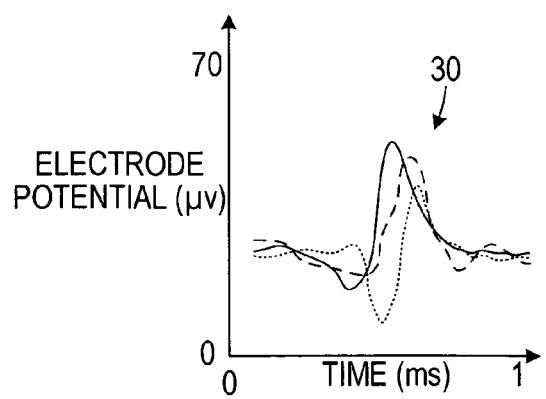
FIG. 3 is an electrode potential vs. time graph of several action potentials.

As shown in FIG. 3, impulses from axons, generate action potentials 30. Different action potentials 30 are denoted by different line patterns. A single electrode may sense several different action potentials, with each action potential corresponding to a different mental task.

Figure 4:
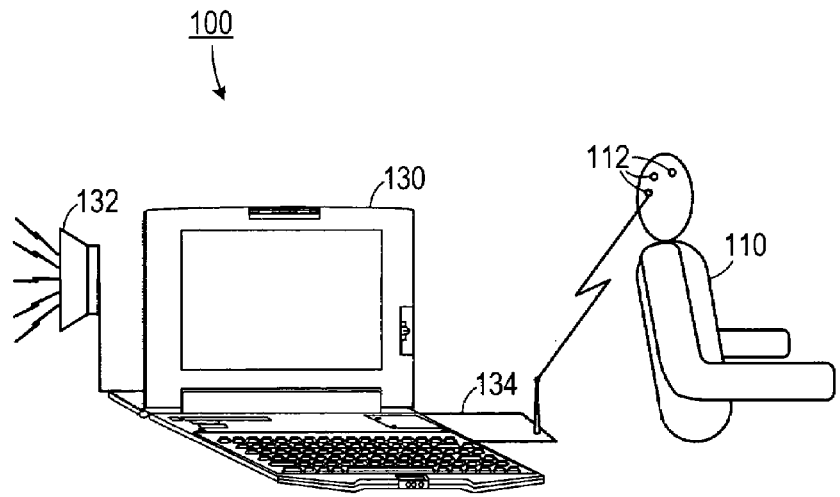
FIG. 4 is a schematic diagram of an apparatus according to the invention.

A typical apparatus is shown in FIG. 4, in which the subject 110 has several electrodes 112 implanted. The electrodes 112 transmit neural impulses via a radio signal to a receiver 134 that is coupled to a computer 130. The receiver 134 may be coupled to the computer 130 through, for example, a PCMCIA card. The computer 130 is programmed to receive a neural impulse, determine which type of neural impulse has been received, find a sound that corresponds to the specific neural impulse and generate the sound through an audio system that includes a speech generator and a speaker 132, or other sound producing device.

The system may detect specific action potentials to generate phonemes, or it may associate patterns of action potentials with phonemes. For example a specific combination of action potentials from one electrode, or several different electrodes, may be paired with a specific phoneme.

Figure 5:
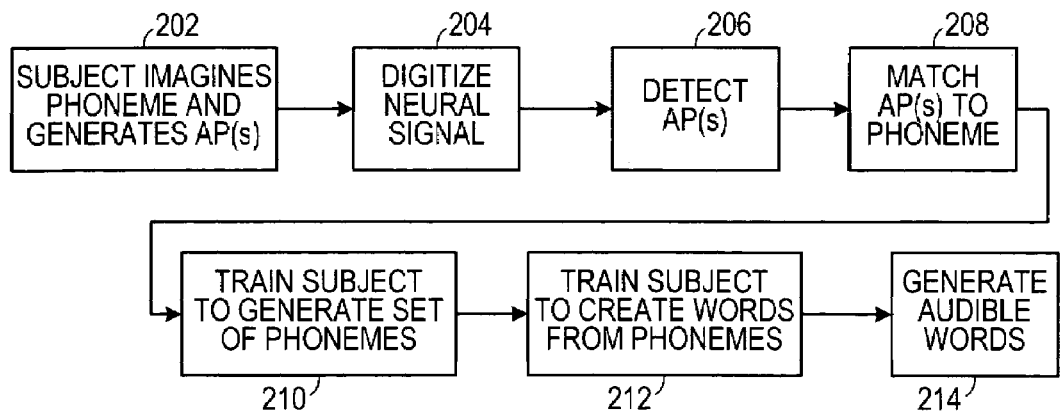
FIG. 5 is a flow diagram of a method according to the invention.

In one speech generating embodiment, as shown in FIG. 5, the subject imagines a phoneme thereby generating one or more action potentials 202. The action potentials (or other neural signals) are digitized and input to the computer 204. The computer detects specific action potentials 206 and matches them to corresponding phonemes 208. The subject is trained to generate a set of phonemes 210 through a feedback process in which the subject imagines saying a phoneme and hears the result from the computer. Through several repetitions, the subject pairs generating specific action potentials with corresponding phonemes. The subject is then trained to generate different phonemes in sequence, thereby creating words 212. At this point, the subject is able to generate audible words 214 and, thereby, communicate with others.

In this embodiment, each neural pulse is linked to the production of a single phoneme. Thus, firing of a single pulse from Broca's area of the brain will result in the production of a single phonemic sound, while the pattern of sequential firings will result in the production of combinations of sounds to form words.

The invention allows direct speech generation from brain activity without the need of an intermediate data input or interface. In one embodiment, the human speech area is localized using functional MRI in speaking and locked-in subjects. Then at least two neurotrophic electrodes are implanted into the brain of the subject. Several robust neural signals are sensed and outputted to a phonemic generator and the subject is trained to control these phonemes until words are intelligible. Learning curves for the production of intelligible speech can be created accordingly. The invention can also include implanting multiple electrodes into the subject, and enlarging the phonemic library while training the subjects to control a diverse and increasing number of phonemes so as to produce an increasing number of words.

While the system may produce phonemes, the system can also pair neural impulses with other sounds, such as specific frequencies or musical notes.

In one experimental application, data from test subject shows that multiple action potentials are available providing adequate data bandwidth (i.e., number of data channels) for production of complex data such as speech. The data was analyzed using the Off-Line Sorter, available from Plexon Inc., Dallas, Tex., a set of tools for signal separation. In the analysis, contour mapping was primarily used. The analog data was digitized and the action potentials were separated in time bins ranging from 1.2 or 4.8 msec depending on pre- and post-wave shape analysis requirements. Each separated action potential was then represented as a point in 2D or 3D space according to a choice of parameters including peak to trough amplitude, peak amplitude or valley amplitude, slice 1 and 2 (the waveform height at a selected point in time), and timestamp (particularly useful in the 3D mode). Having separated the action potentials, a .nex file was created for analysis on the NeuroExplorer (NEX) program. Alternatively, parameter files (.tpl) are created for sorting of other data files. Data files used are from Plexon digitized data (.ddt) and DataWave acquired data (.uff). The NEX program allows analysis in both the time and frequency domains. In the time domain we commonly build rate histograms, interspike interval histograms, peri-event histograms, rasters and crosscorrelograms. In the frequency domain, a power spectral density is built. All these analyses can handle large data sets.

In one experimental embodiment, all MRI experiments were conducted on a 3T whole body scanner (Philips Intera). Blood oxygenation level dependent (BOLD) images were collected using T2* weighted gradient echo planar imaging (EPI) method with TR/TE/angle=3000 ms/40 ms/90°, field of view (FOV) of 240×240 mm and matrix of 96×96 pixels, reconstructed to 128×128. High resolution T1-weighted spin echo anatomical images were collected with TR/TE/angle=500 ms/20 ms/90°, FOV of 240×240 mm and matrix of 256×256 pixels at the same slice locations as EPI. For both T1 weighted imaging and EPI, 28 oblique axial slices approximately parallel to the AC-PC line with 4 mm thickness, 0 gap, was selected to cover the whole brain. In addition, high resolution 3D T1 weighted gradient echo imaging was obtained using isotropic voxel size (1 mm) for surface and volume rendering of the brain in order to better visualize and localize activated brain region and assist surgical plan.

Functional images were processed and analyzed using a statistical parametric mapping algorithm implemented in SPM99 program (produced by the Welcome Department of Cognitive Neurology, London, UK). EPI images were realigned to the first image of the series using a rigid-body transformation procedure, corrected for motion artifacts. The high-resolution T1 and EPI template images were co-registered. A general linear model was applied to the time-course of activation of each voxel to obtain a statistical map. The statistical maps then were extracted at defined threshold and superimposed on the T1 weighted anatomical images. Both functional maps and T1 weighted images were used as references for NE implant surgery. This task has been tested and yielded robust activation in Broca's area.

In one embodiment, the following electrode implantation technique is employed: Immediately prior to surgery, an anatomic MRI is performed with fiducial markers in place on the scalp. After general anesthesia and stabilization of the head, the 3D frameless stereotaxy system is used to localize the target and hence determine the final location of the scalp incision. After standard sterilization of the skin, the scalp is incised and craniotomy performed. The brain is exposed after opening the dura and the final gyral target is localized using the frameless stereotaxy system again. The implant site will be identified in reference to fMRI data. Trophic factor filled Neurotrophic Electrodes (NEs) are approximated to the cortex whose pia has been incised and guided into position under the microscope to a depth of 5 to 6 mms below the cortical surface at an angle of 45 degrees to the planar surface of the gyrus. The outer (or upper) end of the NE is pushed below the surface and then covered with gelfoam until the craniotomy opening is a bed of gelfoam. This is covered with acrylic cement after the NE connectors have been connected to the electronics. All is covered with acrylic and the wound is closed in layers. A drain is usually not utilized.

After the electrodes are implanted and secured to the skull at the craniotomy opening (see below), the electronic module is implanted on the skull and connected to the electrodes. The electronic module contains two or three amplifiers (with about 1,000× gain), FM transmitters and calibration systems. These are powered by a power induction coil with a rectifier and regulator to supply ±5 volts. This avoids implanting batteries and can allow implantation for the lifetime of the subject. The devices are built using surface mount components and covered with insulating Elvax Polymer (DuPont Nemours) covered with a tough Silastic coat for mechanical protection. The system is contoured to the shape of the skull.

Recordings begin when the incision has completely healed usually in about three weeks. The power induction coil is approximated to the scalp over the inner coil and set at its transmission frequency near 1 MHz. Receiving antennae are placed close to the scalp and Win Radio system (available from Win Radio Inc.) used to tune them. The signals are routed to an amplifier with about 10 or 20 times gain and filter settings of 500 to 5,000 Hz for Action potentials. The data is archived on a DDS tape recorder (from Cygnus Inc.) for offline analysis.

Offline data analysis is achieved using Plexon Inc's (Dallas, Tex.) Off-Line Sorter. The results of these analyses provide information on which action potentials fire independently. These can be selected for the online spike sort program.

The output of the Plexon Online Spike Sort program is fed to the PCMCIA card of a laptop computer. It is first channeled to the Plexon computer for online processing that includes signal separation using Plexon Inc's Spike Sort Program. The pulse outputs are directed to the PCMCIA card into our MC software that accepts pulses. The software looks at 50 ms of signal at a time. If a spike is detected within that time period then the phoneme sound byte is triggered. Each sound byte will have an approximate duration of 250 ms. If one or more spikes are detected before the sound byte has finished playing, the sound byte will be repeated immediately to simulate an "extended" sound. If no spikes are detected during the repeated playback, then the output will stop once the sound byte has completed playing. In this manner, a sound will be played for as long as spikes are detected. In this way the duration and playback of each phoneme is determined by the timing of the spikes. Each spike from the Plexon Spike Sorter will be routed into a different channel on the PCMCIA card—ideally, one for each of the phonemes in the English language.

The action potentials with the best match for the three initial sounds are located by looking at their correlations, and then only the best-matched action potentials are selected using the Spike Sort program and they are output to the laptop phonemic generator with auditory feedback to the subject, thus closing the aural feedback loop which is essential for learning. At first, only one action potential will be allowed through and it will produce the phoneme whenever it fires. The subject learns to control the firing at a rhythmic 1 hertz rate, such as to the beat of metronome or other device. When the subject has reached proficiency at a rate of 1 hertz with an error tolerance of about 10%, the subject will be trained to fire the other action potentials, such as those matched to sounds "o" and "u". When the subject has learned these individual tasks, all three sounds will be fed back to the subject, thus closing the aural loop. The rate of the subject learning to "speak" will be dependent on several factors including willingness of the subject to learn, the choice of well matched action potentials, and the "cleanliness" of the sorted spikes.

The English language has 44 phonemes, but not all are needed for intelligible speech production. More Neurotrophic Electrodes can be implanted in the subject over time to allow further phoneme creation.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A method of assisting a subject to generate sounds, comprising the steps of:
   a. training the subject to imagine a predetermined sound;
   b. sensing at least one first neural impulse from a first preselected location in the subject's brain, the first neural impulse generated as a result of the subject imagining the predetermined sound;
   c. associating a first preselected sound with the first neural impulse; and
   d. generating the first preselected sound in an audible format.

2. The method of claim 1, wherein the first preselected sound corresponds to a first phoneme.

3. The method of claim 1, wherein the first preselected sound corresponds to a note of a first frequency.

4. The method of claim 1, wherein the first neural impulse comprises a first action potential.

5. The method of claim 4, further comprising the step of detecting a second action potential detected at the first preselected location of the subject's brain.

6. The method of claim 5, further comprising the step of
   a. associating a second preselected sound, different from the first preselected sound, with the second action potential; and
   b. generating the second preselected sound in an audible format.

7. The method of claim 6, wherein the second preselected sound corresponds to a second phoneme, different from the first phoneme.

8. The method of claim 1, wherein the first neural impulse comprises a local field potential.

9. The method of claim 1, further comprising the step of implanting a neural electrode into the preselected location of the subject's brain, wherein the sensing step comprises sensing the neural impulse at the neural electrode.

10. The method of claim 9, wherein the neural electrode implanting step comprises the step of implanting a neurotrophic electrode.

11. The method of claim 2, further comprising the steps of:
    a. sensing at least one second neural impulse from a second preselected location, different from the first preselected location, of the subject's brain;
    b. associating a second preselected phoneme, different from the first preselected phoneme, with the second neural impulse; and
    c. generating an audible sound corresponding to the second preselected phoneme.

12. The method of claim 11, wherein the second neural impulse comprises a local field potential.

13. The method of claim 11, wherein the second neural impulse comprises an action potential.

14. The method of claim 1, further comprising the steps of:
    a. performing a functional MRI scan of the subject's brain while the subject executes a mental exercise, thereby determining at least one area of brain activity during the mental exercise; and
    b. applying an electrode to the area of brain activity to sense neural impulses.

15. The method of claim 1, wherein the sensing step comprises sensing a preselected set of a plurality of different action potentials at the first preselected location of the subject's brain.

16. A method of assisting a subject to generate speech, comprising the steps of:
    a. training the subject to imagine a predetermined sound;
    b. sensing a plurality of neural impulses from a plurality of locations in the subject's brain generated as a result of the subject imagining the predetermined sound;
    c. associating a preselected sound with a predetermined pattern of neural impulses; and
    d. generating the preselected sound in an audible format.

17. The method of claim 16, wherein the neural impulses comprise action potentials.

18. The method of claim 16, wherein the neural impulses local field potentials.

19. The method of claim 16, wherein the preselected sound comprises a phoneme.

20. The method of claim 16, wherein the preselected sound comprises a frequency.

21. A method of enabling communication with a subject, comprising the steps of:
    a. performing a functional MRI scan of the subject's brain while the subject is executing a predetermined mental exercise so as to determine a first location in the subject's brain where neural activity occurs while the subject is executing the mental exercise;
    b. implanting an electrode in the subject's brain at the first location;
    c. training the subject to associate a desire to express a predetermined phoneme with an action potential generated at the first location in the subject's brain;
    d. sensing the action potential at the electrode; and
    e. generating an audible sound corresponding to the predetermined phoneme in response to the sensing of the action potential.

22. The method of claim 21, further comprising the steps of:
   a. determining at least one second location in the subject's brain where neural activity occurs while the subject is executing a portion of the mental exercise;
   b. implanting a second electrode in the subject's brain at the second location;
   c. training the subject to associate a desire to express second predetermined phoneme with a second action potential generated at the second location in the subject's brain;
   d. sensing the second action potential; and
   e. generating a second audible sound corresponding to the second predetermined phoneme in response to the sensing of the second action potential.

23. The method of claim 21, further comprising the steps of:
   a. training the subject to associate a desire to express second predetermined phoneme with a second action potential generated at the first location in the subject's brain;
   b. sensing the second action potential; and
   c. generating a second audible sound corresponding to the second predetermined phoneme in response to the sensing of the second action potential.

24. An apparatus for assisting a subject to generate speech based upon electrical activity in the brain, comprising:
   a. at least one sensor that senses a neural impulse in the subject's brain, which has been generated after the subject has been trained to generate the neural impulse in association with a desire to express a phoneme, and that generates a signal representative thereof;
   b. an electronic speech generator that generates the phoneme in response to the generation of the signal; and
   c. an audio system that generates audible sounds corresponding to the phoneme based upon the signal received from the speech generator.

25. The apparatus of claim 24, wherein the neural impulse comprises a local field potential.

26. The apparatus of claim 24, wherein the neural impulse comprises a neuronal discharge.

27. The apparatus of claim 24, wherein the neural impulse comprises an action potential.

28. The apparatus of claim 27, wherein the sensor is capable of sensing a plurality of action potentials in the subject's brain and is capable of generating a corresponding plurality of signals, each representative of a different one of the plurality of action potentials, and wherein the electronic speech generator generates a different phoneme in response to each of the plurality of signals, so that the audio system is capable of generating audible sounds that correspond to a plurality of different phonemes in a sequence.

29. The apparatus of claim 24, wherein the sensor comprises an implanted electrode.

30. The apparatus of claim 29, wherein the implanted electrode comprises a neurotrophic electrode.

31. The apparatus of claim 24, wherein the electronic speech generator comprises a computer programmed to detect an action potential sensed by the sensor.

32. The apparatus of claim 31, wherein the computer is further programmed to associate an action potential with a specific phoneme.

33. The apparatus of claim 32, wherein the computer is further programmed to generate audible sounds that correspond to the specific phoneme.

* * * * *